US011627948B2

(12) United States Patent
Brisson et al.

(10) Patent No.: US 11,627,948 B2
(45) Date of Patent: Apr. 18, 2023

(54) SYSTEMS AND METHODS FOR INSTRUMENT ENGAGEMENT

(71) Applicant: INTUITIVE SURGICAL OPERATIONS, INC., Sunnyvale, CA (US)

(72) Inventors: Gabriel F. Brisson, Sunnyvale, CA (US); Gregory W. Dachs, II, San Mateo, CA (US); Niels Smaby, Palo Alto, CA (US); Melody Wu, Sunnyvale, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 35 days.

(21) Appl. No.: 17/142,087

(22) Filed: Jan. 5, 2021

(65) Prior Publication Data
US 2021/0121164 A1  Apr. 29, 2021

Related U.S. Application Data

(63) Continuation of application No. 15/735,082, filed as application No. PCT/US2016/037003 on Jun. 10, 2016, now Pat. No. 10,912,544.
(Continued)

(51) Int. Cl.
*A61B 17/00* (2006.01)
*A61B 34/35* (2016.01)
(Continued)

(52) U.S. Cl.
CPC .............. *A61B 17/00* (2013.01); *A61B 34/35* (2016.02); *A61B 2017/00477* (2013.01); *A61B 2034/302* (2016.02); *A61B 2090/066* (2016.02)

(58) Field of Classification Search
CPC ... A61B 17/00; A61B 34/35; A61B 2090/066; A61B 34/30; A61B 34/70; A61B 90/00
See application file for complete search history.

(56) References Cited

U.S. PATENT DOCUMENTS 5,797,900 A   8/1998 Madhani et al.
7,524,320 B2  4/2009 Tierney et al.
(Continued)

FOREIGN PATENT DOCUMENTS

KR  20110032444 A   3/2011
WO  WO-2007075864 A1  7/2007
(Continued)

OTHER PUBLICATIONS

Extended European Search Report for Application No. EP16808433.3, dated Nov. 23, 2018, 5 pages (ISRG07550/EP).
(Continued)

Primary Examiner — Bickey Dhakal
(74) Attorney, Agent, or Firm — Haynes and Boone, LLP

(57) ABSTRACT

A medical system includes a control system and an instrument manipulator. The instrument manipulator is configured to receive an instrument and includes a first drive output and a first actuating element configured to drive movement of the first drive output. The first drive output is configured to drive a first input coupling of the instrument. The control system is configured to receive an indication that the first input coupling of the instrument is positioned adjacent to the first drive output of the manipulator, in response to receiving the indication, command the first actuating element to cause movement of the first drive output, receive a feedback associated with a force experienced by the first actuating element during the movement of the first drive output,
(Continued)

determine an instruction signal for the first actuating element based on the feedback, and transmit the instruction signal to the first actuating element.

21 Claims, 7 Drawing Sheets

Related U.S. Application Data

(60) Provisional application No. 62/174,204, filed on Jun. 11, 2015.

(51) Int. Cl.
*A61B 34/30* (2016.01)
*A61B 90/00* (2016.01)

(56) References Cited

U.S. PATENT DOCUMENTS

| | | | |
|---|---|---|---|
| 7,963,913 B2 | 6/2011 | Devengenzo et al. | |
| 8,918,211 B2 | 12/2014 | Diolaiti et al. | |
| 9,043,027 B2 * | 5/2015 | Durant | A61B 34/74 700/250 |
| 10,595,836 B2 * | 3/2020 | Smaby | A61B 34/35 |
| 10,912,544 B2 | 2/2021 | Brisson et al. | |
| 2005/0119527 A1* | 6/2005 | Banik | A61B 1/0016 600/117 |
| 2011/0015650 A1 | 1/2011 | Choi et al. | |
| 2013/0325034 A1 | 12/2013 | Schena et al. | |
| 2014/0069437 A1 | 3/2014 | Reis et al. | |
| 2015/0224639 A1* | 8/2015 | Dockter | B25J 3/04 700/264 |
| 2016/0361126 A1 | 12/2016 | Schena et al. | |
| 2016/0361131 A1 | 12/2016 | Dachs, II et al. | |
| 2017/0172672 A1 | 6/2017 | Bailey et al. | |
| 2020/0029945 A1 | 1/2020 | Brisson et al. | |
| 2020/0054401 A1 | 2/2020 | Yu et al. | |

FOREIGN PATENT DOCUMENTS

| | | |
|---|---|---|
| WO | WO-2009151205 A1 | 12/2009 |
| WO | WO-2010126128 A1 | 11/2010 |
| WO | WO-2010126129 A1 | 11/2010 |
| WO | WO-2011037394 A2 | 3/2011 |
| WO | WO-2015023834 A1 | 2/2015 |
| WO | WO-2015023853 A1 | 2/2015 |
| WO | WO-2015142785 A1 | 9/2015 |
| WO | WO-2015142788 A1 | 9/2015 |
| WO | WO-2015142789 A1 | 9/2015 |
| WO | WO-2015142791 A1 | 9/2015 |
| WO | WO-2015142792 A1 | 9/2015 |
| WO | WO-2015142793 A1 | 9/2015 |
| WO | WO-2015142795 A1 | 9/2015 |
| WO | WO-2015142889 A1 | 9/2015 |
| WO | WO-2015142958 A1 | 9/2015 |
| WO | WO-2015153642 A1 | 10/2015 |

OTHER PUBLICATIONS

International Search Report and Written Opinion for Application No. PCT/US16/37003, dated Oct. 12, 2016, 20 pages (ISRG07550/PCT).

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

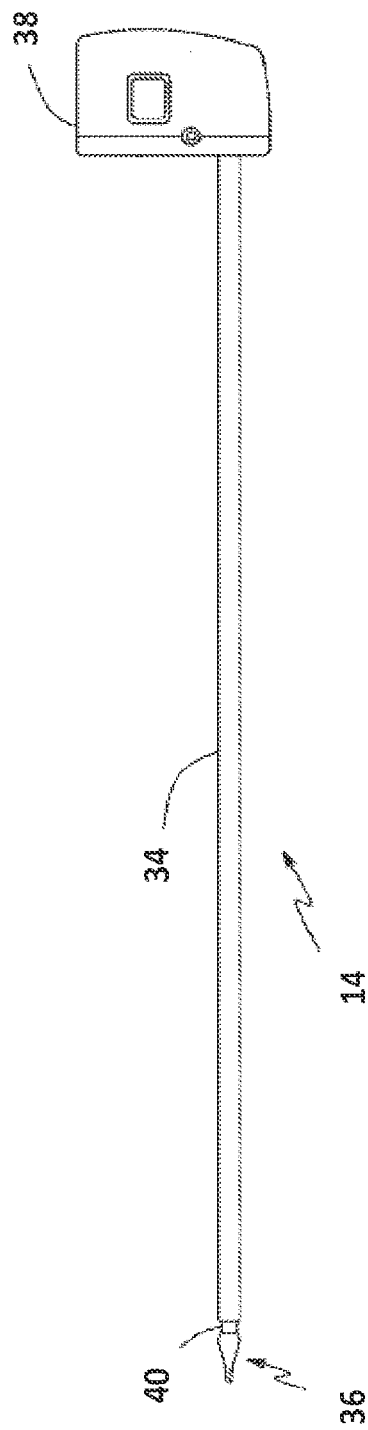

US 11,627,948 B2

SYSTEMS AND METHODS FOR INSTRUMENT ENGAGEMENT

RELATED APPLICATIONS

This patent application is a continuation of U.S. application Ser. No. 15/735,082 filed Dec. 8, 2017, which claims priority to and the benefit of the U.S. national phase of International Application No. PCT/US2016/037003, filed Jun. 10, 2016, which designated the U.S. and claims priority to and the benefit of the filing date of U.S. Provisional Patent Application 62/174,204, entitled "SYSTEMS AND METHODS FOR INSTRUMENT ENGAGEMENT," filed Jun. 11, 2015, all of which are incorporated by reference herein in their entireties.

FIELD

The present disclosure is directed to systems and methods for mechanical engagement, and more particularly to systems and methods for confirming that a drive coupling has successfully engaged with an input coupling.

BACKGROUND

Many mechanical systems make use of motors that move objects into different positions. In general, an actuating element, such as a motor, has a drive output that mates with an input coupling of a tool to be actuated. Various mechanical structures may be used to engage the drive output with the input coupling. One example is a boss and pocket structure. Specifically, the drive output may include a disc that has a boss extending from the surface of the disc. The boss may be designed to fit into a corresponding pocket on a disc connected to the input coupling. When the boss is successfully positioned within the pocket, rotation of the drive output causes rotation of the input coupling, which in turn causes movement of the tool.

A mechanical system that involves engaging a drive output with an input coupling may be a teleoperative medical system used to perform a medical procedure. The teleoperative medical system may include motors with drive outputs that couple to and operate interchangeable medical instruments. In some embodiments, the drive outputs of the motors include drive discs that engage with corresponding instrument discs on the medical instrument. Each of the instrument discs may actuate a different type of motion in the medical instrument. For example, one disc may control actuating members that change the roll position of the instrument. Other discs may control actuating members that change the yaw, pitch, or grip of the medical instrument. When an interchangeable instrument is connected to the teleoperative medical system, each of the drive discs is engaged with a corresponding instrument disc to drive movement of the medical instrument as desired.

If the drive outputs are not properly engaged with the input couplings, the medical instrument may not respond correctly to user commands transmitted through the teleoperative medical system. An improper coupling may require removal and reattachment of the medical instrument to the drive outputs, creating inefficiencies in the medical procedure.

SUMMARY

The embodiments of the invention are summarized by the claims that follow below.

In one embodiment, a method of engaging a medical instrument with a medical instrument manipulator comprises receiving an indication that a first input coupling of the medical instrument is positioned adjacent to a first drive output of the manipulator. The first drive output is driven by a first actuating element. In response to receiving the indication, the first drive output is rotated in a first rotational direction. A determination is made, by one or more processors, as to whether a resistance torque is experienced by the first actuating element after rotating the first drive output in the first rotational direction. If the resistance torque is not experienced by the first actuating element after the rotating of the first drive output in the first rotational direction, the first drive output is rotated in a second rotational direction. A determination is made, by the one or more processors, as to whether a resistance torque is experienced by the first actuating element after the rotating of the first drive output in the second rotational direction.

In another embodiment, a computer-assisted medical device comprises one or more processors, a medical instrument manipulator, and a medical instrument. The computer-assisted medical device is configured to engage the medical instrument with the medical instrument manipulator by receiving an indication that a first input coupling of the medical instrument is positioned adjacent to a first drive output of the manipulator. The first drive output is driven by a first actuating element. In response to receiving the indication, the first drive output is rotated in a first rotational direction. A determination is made, by one or more processors, as to whether a resistance torque is experienced by the first actuating element after rotating the first drive output in the first rotational direction. If the resistance torque is not experienced by the first actuating element after the rotating of the first drive output in the first rotational direction, the first drive output is rotated in a second rotational direction. A determination is made, by the one or more processors, as to whether a resistance torque is experienced by the first actuating element after the rotating of the first drive output in the second rotational direction.

In another embodiment, a non-transitory machine-readable medium comprises a plurality of machine-readable instructions which when executed by one or more processors associated with a computer-assisted medical device are adapted to cause the one or more processors to perform a method. The method comprises rotating, in a first rotational direction, a first drive output of a manipulator portion of the computer-assisted medical device. The first drive output being driven by a first actuating element. The method further includes determining whether a resistance torque is experienced by the first actuating element after rotating the first drive output in the first rotational direction. The resistance torque signals an engagement of a first input coupling of a medical instrument with the first drive output. The method further includes rotating the first drive output in a second rotational direction on the condition that the resistance torque is not experienced by the first actuating element after the rotation of the first drive output in the first rotational direction. The method further includes determining whether a resistance torque is experienced by the first actuating element after the rotation of the first drive output in the second rotational direction, wherein the resistance torque signals an engagement of the first input coupling of a medical instrument with the first drive output.

In another embodiment, a method of engaging a medical instrument with a medical instrument manipulator comprises receiving an indication that a first input coupling of the medical instrument is positioned adjacent to a first drive output of the manipulator. The first drive output is driven by a first actuating element. In response to receiving the indication, rotating the first drive output in a first rotational direction according to a preprogrammed rotation protocol. The method further includes determining, by one or more processors, whether a resistance torque is experienced by the first actuating element after rotating the first drive output in the first rotational direction according to a preprogrammed rotation protocol. The method further includes terminating the preprogrammed rotation protocol on the condition that the resistance torque is experienced by the first actuating element.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

FIG. 3 illustrates the instrument of FIG. 2 in greater detail.

DETAILED DESCRIPTION

Figure 1:
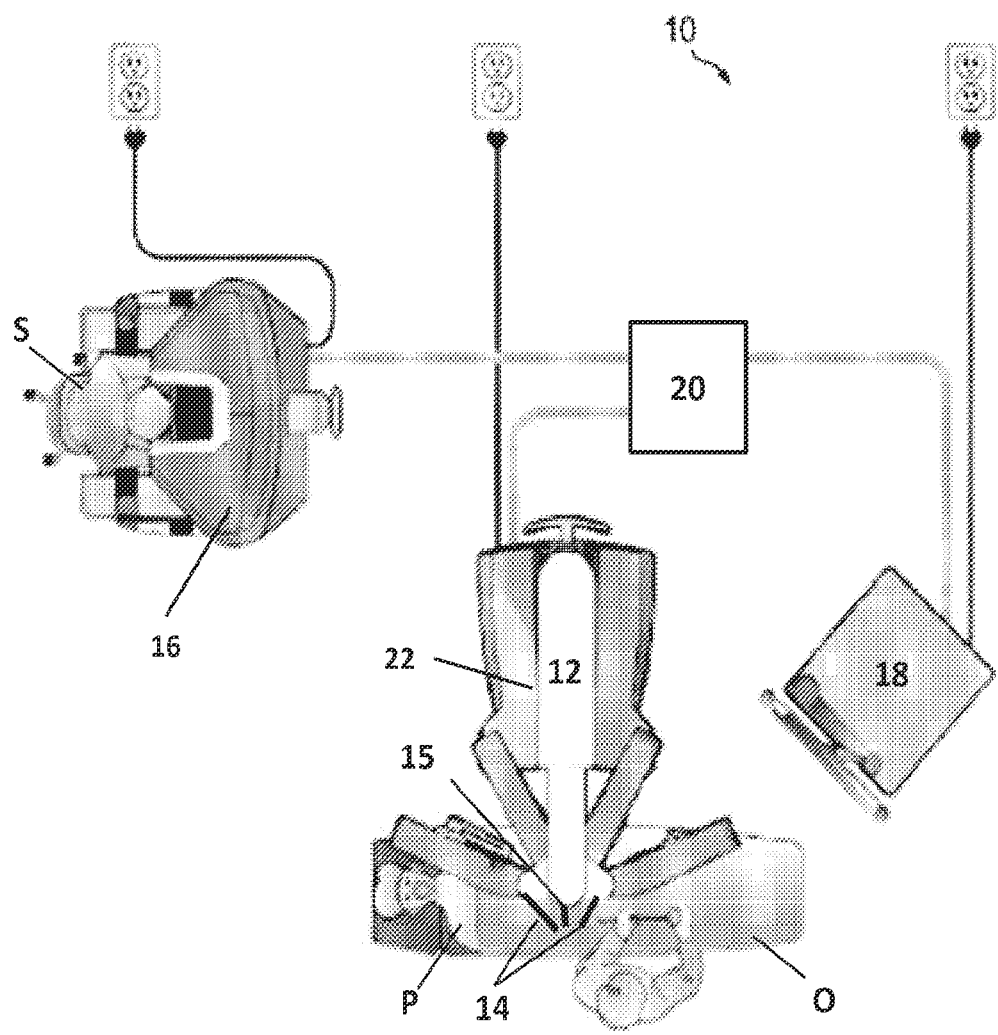
FIG. 1 is a plan view of a minimally invasive teleoperative medical system being used to perform a surgery, in accordance with many embodiments.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention.

Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment can be used or omitted as applicable from other illustrative embodiments. For the sake of brevity, the numerous iterations of these combinations will not be described separately. For simplicity, in some instances the same reference numbers are used throughout the drawings to refer to the same or like parts.

Figure 2:
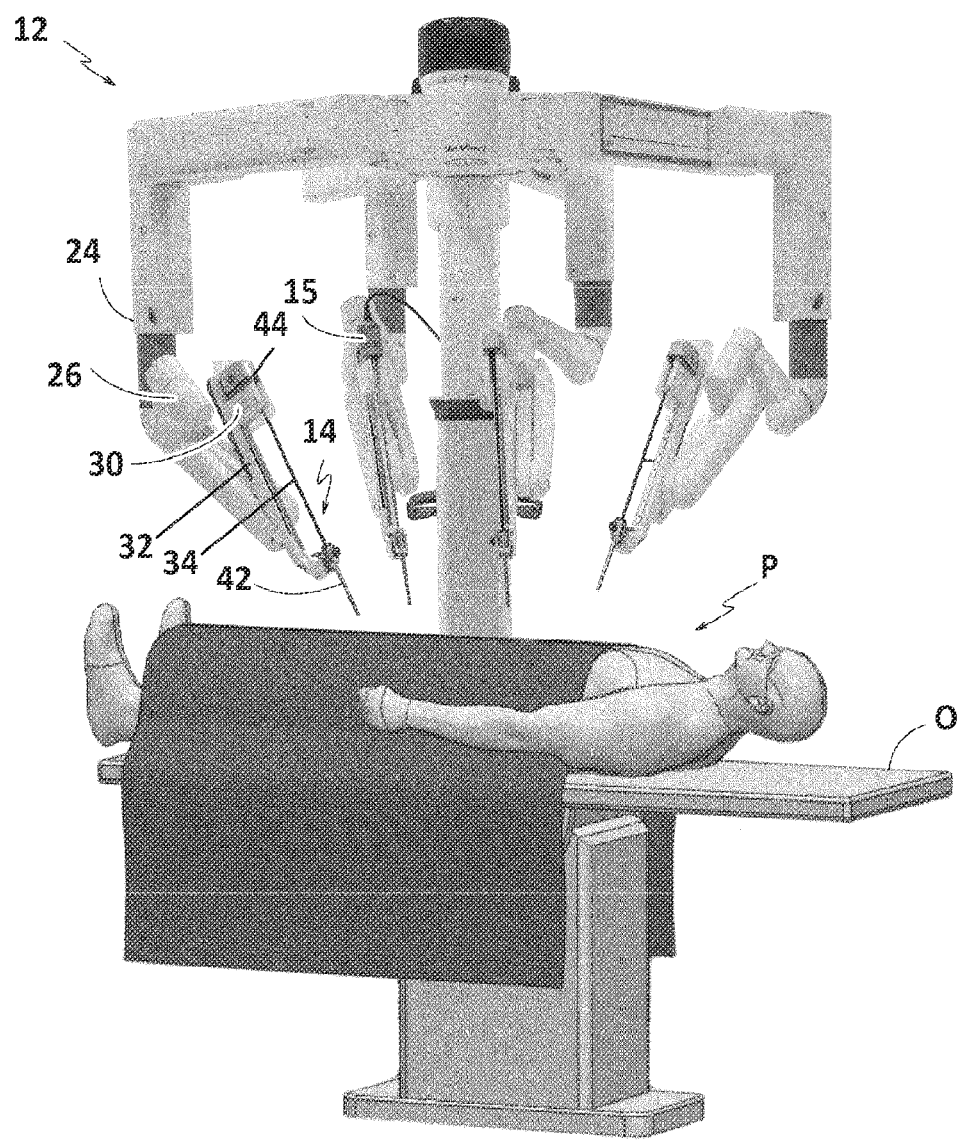
FIG. 2 is a perspective view of a surgeon's control console for a teleoperative medical system, in accordance with many embodiments.

Referring to FIGS. 1 and 2 of the drawings, a teleoperational medical system for use in, for example, medical procedures including diagnostic, therapeutic, or surgical procedures, is generally indicated by the reference numeral 10. As will be described, the teleoperational medical systems of this disclosure are under the teleoperational control of a surgeon. In alternative embodiments, a teleoperational medical system may be under the partial control of a computer programmed to perform the procedure or sub-procedure. In still other alternative embodiments, a fully automated medical system, under the full control of a computer programmed to perform the procedure or sub-procedure, may be used to perform procedures or sub-procedures. As shown in FIG. 1, the teleoperational medical system 10 generally includes a teleoperational assembly 12 mounted to or near an operating table O on which a patient P is positioned. The teleoperational assembly 12 may be referred to as a patient side cart. A medical instrument system 14 and an endoscopic imaging system 15 are operably coupled to the teleoperational assembly 12. An operator input system 16 allows a surgeon or other type of clinician S to view images of or representing the surgical site and to control the operation of the medical instrument system 14 and/or the endoscopic imaging system 15.

The operator input system 16 may be located at a surgeon's console, which is usually located in the same room as operating table O. It should be understood, however, that the surgeon S can be located in a different room or a completely different building from the patient P. Operator input system 16 generally includes one or more control device(s) for controlling the medical instrument system 14. The control device(s) may include one or more of any number of a variety of input devices, such as hand grips, joysticks, trackballs, data gloves, trigger-guns, hand-operated controllers, voice recognition devices, touch screens, body motion or presence sensors, and the like. In some embodiments, the control device(s) will be provided with the same degrees of freedom as the medical instruments of the teleoperational assembly to provide the surgeon with telepresence, the perception that the control device(s) are integral with the instruments so that the surgeon has a strong sense of directly controlling instruments as if present at the surgical site. In other embodiments, the control device(s) may have more or fewer degrees of freedom than the associated medical instruments and still provide the surgeon with telepresence. In some embodiments, the control device (s) are manual input devices which move with six degrees of freedom, and which may also include an actuatable handle for actuating instruments (for example, for closing grasping jaws, applying an electrical potential to an electrode, delivering a medicinal treatment, and the like). An electronics cart 18 can be used to process the images of the surgical site for subsequent display to the surgeon S through the surgeon's console 16.

The teleoperational medical system 10 also includes a control system 20. The control system 20 includes at least one memory and at least one processor (not shown), and typically a plurality of processors, for effecting control between the medical instrument system 14, the operator input system 16, and an electronics system 18. The control system 20 also includes programmed instructions (e.g., a computer-readable medium storing the instructions) to implement some or all of the methods described in accordance with aspects disclosed herein. While control system 20 is shown as a single block in the simplified schematic of FIG. 1A, the system may include two or more data processing circuits with one portion of the processing optionally being performed on or adjacent the teleoperational assembly 12, another portion of the processing being performed at the operator input system 16, and the like. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 20 supports wireless communication protocols such as Bluetooth. IrDA, HomeRF, IEEE 802.11, DECT, and Wireless Telemetry.

In some embodiments, control system 20 may include one or more servo controllers that receive force and/or torque feedback from the medical instrument system 14. Responsive to the feedback, the servo controllers transmit signals to the operator input system 16. The servo controller(s) may also transmit signals instructing teleoperational assembly 12 to move the medical instrument system(s) 14 and/or endoscopic imaging system 15 which extend into an internal surgical site within the patient body via openings in the body. Any suitable conventional or specialized servo controller may be used. A servo controller may be separate from, or integrated with, teleoperational assembly 12. In some embodiments, the servo controller and teleoperational assembly are provided as part of a teleoperational arm cart positioned adjacent to the patient's body.

The teleoperational medical system 10 may further include optional operation and support systems (not shown) such as illumination systems, steering control systems, irrigation systems, and/or suction systems. In alternative embodiments, the teleoperational system may include more than one teleoperational assembly and/or more than one operator input system. The exact number of manipulator assemblies will depend on the surgical procedure and the space constraints within the operating room, among other factors. The operator input systems may be collocated or they may be positioned in separate locations. Multiple operator input systems allow more than one operator to control one or more manipulator assemblies in various combinations.

The teleoperational assembly 12 supports and manipulates the medical instrument systems 14 while the surgeon S views the surgical site through the console 16. An image of the surgical site can be obtained by the endoscopic imaging system 15, such as a stereoscopic endoscope, which can be manipulated by the teleoperational assembly 12 to orient the endoscope 15. The number of medical instrument systems 14 used at one time will generally depend on the diagnostic or surgical procedure and the space constraints within the operating room among other factors. The teleoperational assembly 12 may include a kinematic structure of one or more non-servo controlled links 24 (e.g., one or more links that may be manually positioned and locked in place, generally referred to as a set-up structure) and a teleoperational manipulator 26. An instrument carriage 30 travels linearly along an instrument spar 32. As shown also in FIG. 3, the medical instrument system 14 includes an instrument shaft 34, a surgical tool 36, and a proximal control portion 38. The instrument shaft 34 and the surgical tool 36 are controlled by a jointed wrist 40 that allows the orientation of the surgical tool 36 to be manipulated with reference to the shaft 34. The surgical tool 36 may be any of a variety of surgical tools including forceps, a needle driver, a cautery device, a cutting tool, an imaging tool (e.g., an ultrasound probe), or a combined device that includes a combination of two or more various tools and imaging devices. The surgical tool may include one piece devices such as cutting instruments or may include two or other multi-piece devices such as scissors or gripping tools. Surgical instruments that are used with the invention may control their surgical tools with a plurality of rods and/or flexible actuating cables extending within the shaft 34 and be able to bend as they pass through the wrist joint 40. A cannula 42 is coupled to a distal end of the instrument spar 32 and is sized to receive the shaft 34.

In order to provide a sterile operation area while using a teleoperated surgical system, a barrier may be placed between the non-sterile system and the sterile surgical field. Therefore, a sterile component 44, such as an instrument sterile adapter (ISA), is placed between the surgical instrument 14 and the instrument carriage 30. The placement of an instrument sterile adapter between the surgical instrument 14 and the carriage 30 provides a sterile coupling point for the surgical instrument 14 and the carriage 30. This permits removal of surgical instruments from the carriage 30 and exchange with other surgical instruments during the course of a surgery.

Figure 4B:
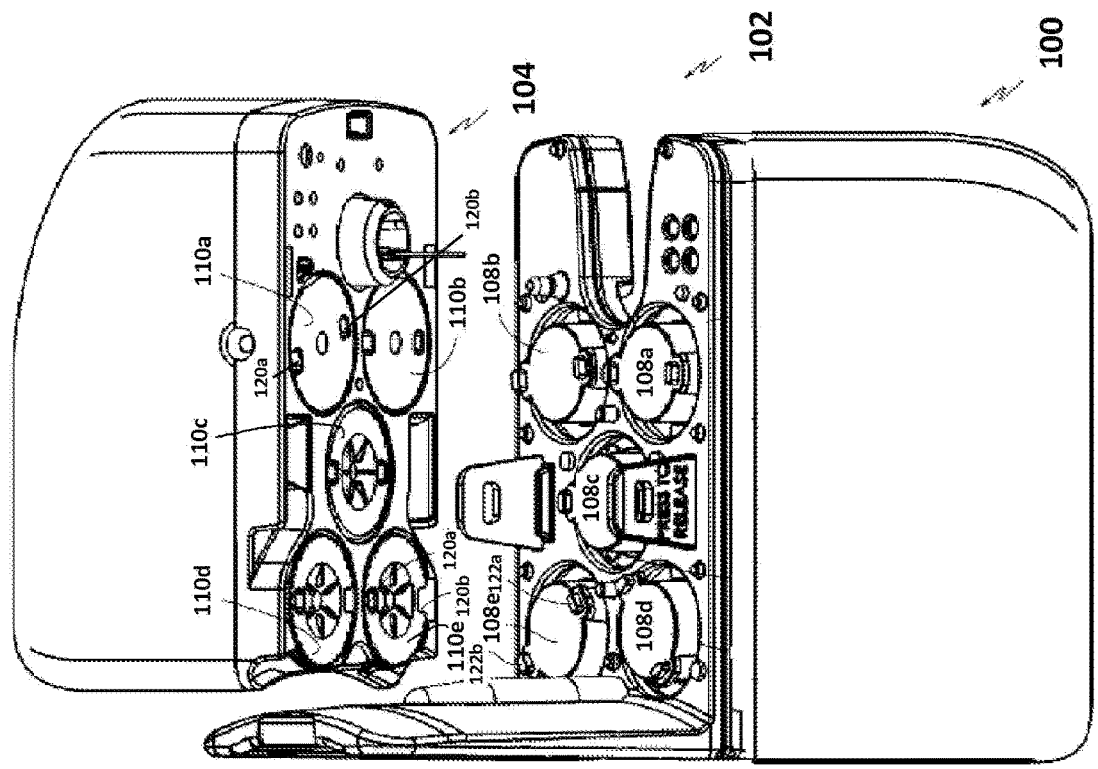
FIGS. 4A and 4B are partially exploded views of a surgical instrument coupling portion, an instrument sterile adaptor, and a portion of a carriage of an instrument manipulator.
Figure 4A:
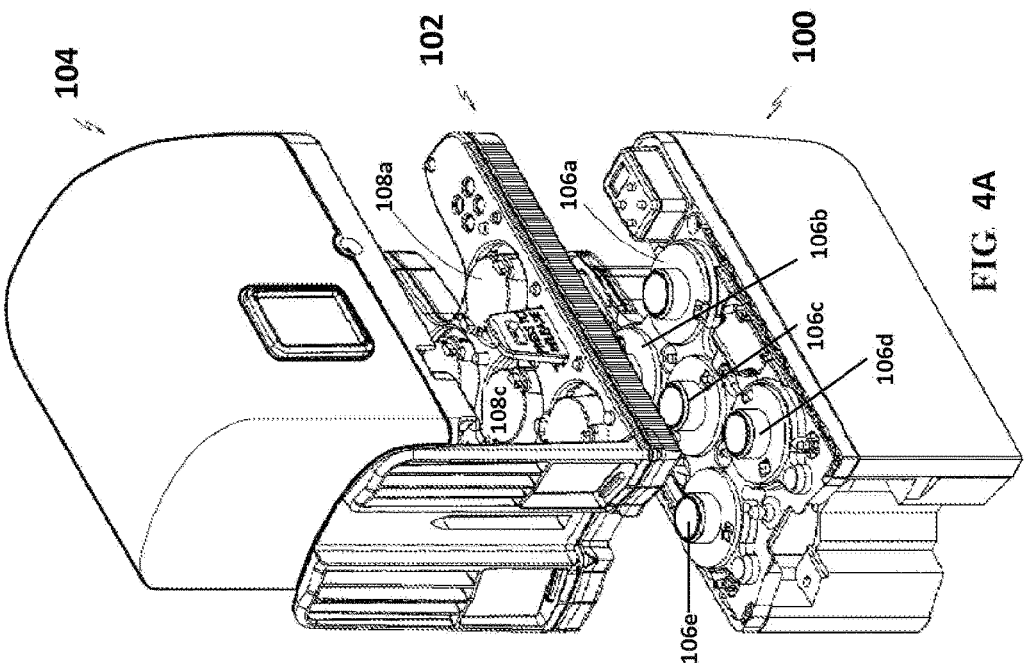

FIG. 4A shows a partially exploded view of the coupling of a carriage 100 (e.g. carriage 30), an ISA 102 (e.g., ISA 44), and an instrument proximal control portion 104 (e.g., proximal control portion 38). In one embodiment, as shown in FIG. 4B, the first stage of the coupling process includes the ISA 102 coupling with the carriage 100. Carriage drive outputs, which in this embodiment are drive discs 106a-e, on the carriage 100 are rotated to engage the corresponding ISA output couplings 108a-e, respectively. The ISA output couplings, which in this embodiment are ISA discs 108a-e, are rotated by the drive discs 106a-e, respectively, to engage corresponding instrument input couplings 110a-e of the instrument proximal control portion 104. In this embodiment, the instrument input couplings are instrument discs 110a-e. The instrument carriage 100 houses actuating elements (e.g., motors) for driving movement of each carriage drive disc 106a-e. The ISA and ISA coupling to the carriage is described in detail in U.S. Pat. App. No. 62/103,991 filed Jan. 15, 2015 (disclosing "Coupler to Transfer Motion to Surgical Instrument from Teleoperated Actuator"), which is incorporated by reference herein in its entirety. The carriage drive outputs are described in detail in U.S. Pat. App. No. 61/954,408 filed Mar. 17, 2014) (disclosing "Systems and Methods for Confirming Disc Engagement"), which is incorporated by reference herein in its entirety.

In this embodiment, the instrument input couplings 110a-e are disc-shaped and each includes a pair of pockets 120a, 120b, respectively. In this embodiment, the pockets 120a, 120b are located at 180 degrees from each other. In alternative embodiments, there may be fewer or more pockets arranged with various other spacings. Each of the ISA output couplings 108a-e are disc-shaped and each includes a pair of bosses 122a, 122b. In this embodiment, the bosses 122a, 122b may be positioned near the circumference of the discs, at 180 degrees from each other. Each boss is sized and shaped to seat within a corresponding pocket. For example, the bosses 122a, 122b on the ISA disc 108e are sized and shaped to seat within the pockets 120a. 120b, respectively, of the instrument disc 110e. In alternative embodiments, there may be fewer or more bosses arranged with various other spacings. In various other embodiments, a sterile adaptor may be omitted and the instrument drivers may be directly coupled to the carriage drivers. In various other embodiments, the boss and pocket configuration may be switched with the boss protruding from the instrument disc and with a pocket in the ISA disc.

In the embodiment of FIGS. 4A and 4B, the ISA includes five discs. The instrument may be designed to use any number of the ISA discs to control motion of the instrument. For example, one instrument may use only three of the discs to control operation of the instrument. Another instrument may use all five discs. The different ISA discs may be used to drive different types of movement of the instrument. For example, the disc 108d may be used to control the roll of the instrument about the instrument's axis. The disc 108c (alone or in combination with other discs) may be used to control the pitch of the surgical tool by movement of the wrist. A coordinated motion of the discs 108a, 108b, 108e may be used to control the yaw of the wrist and surgical tool. A different coordinated motion of the disc 108a and the disc 108b may be used to control grip of the instrument. Each of these discs can be checked for proper engagement using the principles described above.

For the teleoperational assembly to control operation of an instrument, the instrument proximal control portion 104 is attached to the ISA 102, thus placing the set of ISA coupling discs 108a-e adjacent to the instrument driver discs 110a-e, respectively. When the discs 108a-e are first placed adjacent to the instrument discs 110a-e, the discs may not be aligned to the proper rotational positions such that the bosses will slide into the pockets. To achieve full engagement between the bosses and their respective pockets, an instrument engagement procedure may be conducted.

Full engagement between the bosses and the pockets for each disc coupling allows the medical instrument to operate with a full range of motion. In existing systems, engagement procedures may have inefficiencies. For example, in existing systems the actuating element coupled to each drive disc may be programmed to cause the ISA disc to rotate for multiple single direction revolutions (e.g. 2 or 3 preprogrammed single direction revolutions) until both bosses slide into the corresponding pockets of the instrument drive disc, thus completing the engagement. Requiring multiple preprogrammed single direction revolutions for multiple disc engagements, performed in serial, may be inefficient and time consuming. Existing systems may have no ability to sense engagement and abort the preprogrammed single direction revolution engagement protocol if engagement is determined prior to the completion of the protocol. In existing systems, rotating the ISA disc for the preprogrammed multiple single direction revolutions, may still not achieve engagement. If engagement is not achieved, the operator must detach the instrument from the ISA, reattach the instrument to the ISA, and initiate the engagement procedure from the beginning. Repeating the engagement procedure may be time-consuming and burdensome to the operator. Investigations have shown that at least one cause of engagement failures in existing systems is constraint of the ISA discs. The ISA disc, when coupled to the carriage drive discs, is strongly constrained. That is, the spatial orientation of the ISA disc, which may function as an Oldham-style coupling, is generally limited a single translational degree of freedom, unable to tilt or translate in multiple dimensions. Because of this constraint, slight design variations (e.g. bosses of slightly different lengths or slight instrument tilt) may contribute to engagement failures. More specifically, a slight misalignment between the ISA disc and the instrument disc will cause the ISA bosses to arrive at the instrument pockets at slightly different times. If the bosses are of slightly different lengths or if the instrument is tilted, the first boss to reach a first pocket may not actually contact the instrument disc and fall into the first pocket. Rather, it may move just past the first pocket. When the second boss reaches the second pocket and begins to fall in to the second pocket, contact of the second boss with the second pocket may nudge the instrument disc in its translational degree of freedom, causing the first pocket to move further away from the first boss. Thus, the first boss is unable to drop into the first pocket of the instrument disc as the ISA disc continues to rotate in the first rotational direction.

The various engagement procedures that follow may minimize or eliminate the inefficiencies associated with the engagement procedures for existing systems. These engagement procedures may allow disc engagement to be detected earlier than in existing procedures, thus shaving critical time from the engagement process. These procedures allow the ISA disc to rotate in an opposite direction from the initial direction of rotation, if engagement is not detected on the initial direction of rotation. Reversing the direction of the rotation may help alleviate the problem of ISA disc constraint because reverse movement of one engaged boss will nudge the instrument disc, causing the unoccupied pocket to move toward the second ISA boss. An engagement procedure that provides rotation in both directions may decrease the failure rate and require fewer reinstallations by the user.

Figure 5:
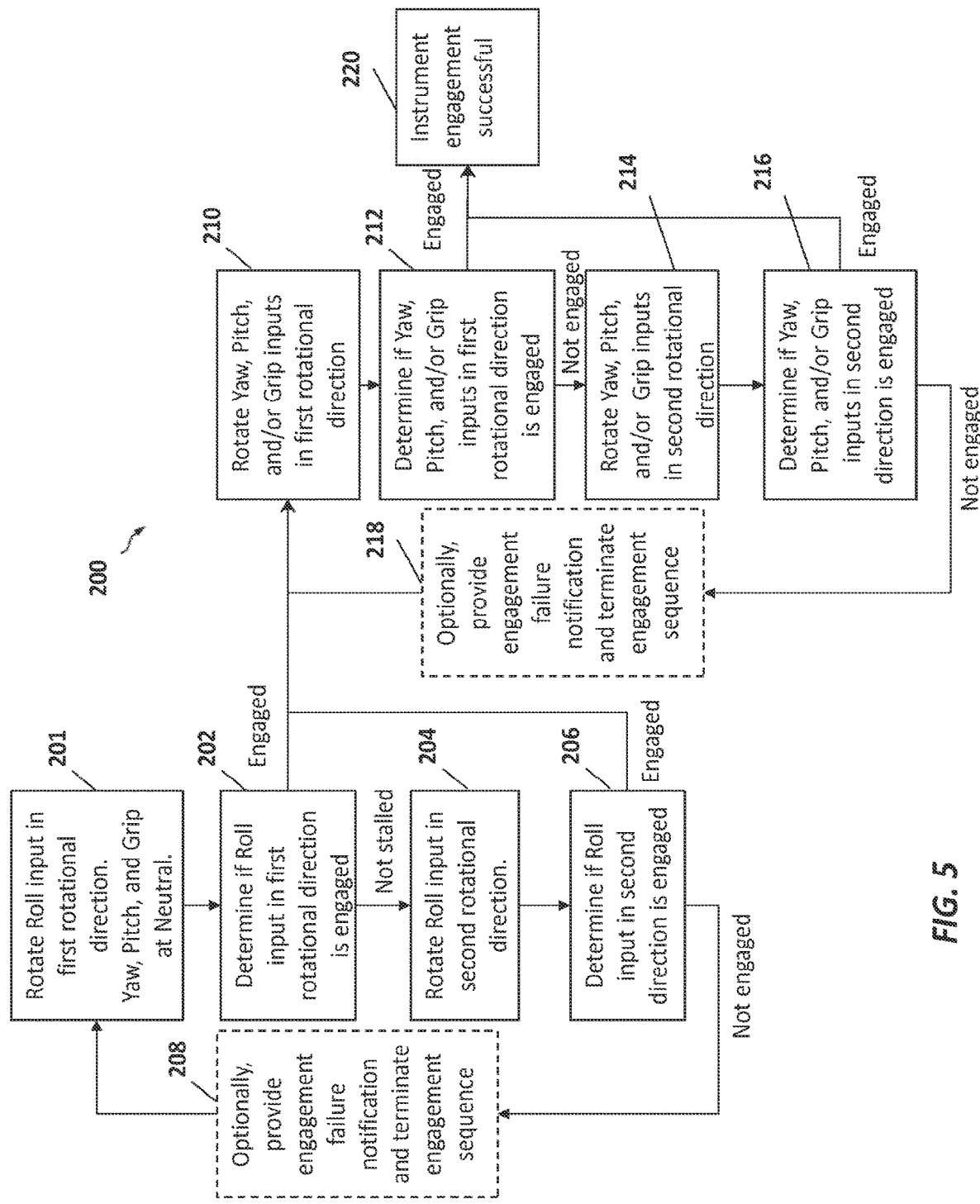
FIG. 5 is a flowchart showing an illustrative method for instrument engagement, according to one example of principles described herein.

FIG. 5 is a flowchart 200 showing an illustrative method for instrument engagement. The instrument engagement procedure is initiated after the proximal control portion of the instrument is attached to the ISA and the ISA discs are placed adjacent to the instrument discs. The control system may receive a signal or other indication that this attachment has occurred. In this embodiment, the instrument to be engaged may be any wristed instrument that has a gripping function. For example, this engagement procedure may be suitable for use with a needle driver (e.g. a large needle driver (LND)), forceps, a shears, a bipolar cauterizer, or a tissue stabilizer or retractor.

At a process 201, a first ISA disc is rotated in a first rotational direction. In this embodiment, the first ISA disc may be the disc 108d associated with the control of roll motion for the instrument shaft. In alternative embodiments, ISA discs for controlling other operational degrees of freedom of the instrument may be engaged first in the instrument engagement procedure. In alternative embodiments, the ISA may be omitted and the carriage drive discs may directly engage the instrument discs using the described engagement procedures. During process 201, as the roll ISA disc is rotated in the first rotational direction, the other ISA discs (e.g., those controlling yaw, pitch, and grip) are unengaged. They may, for example, be outside the instrument disc range of motion and/or movable to a preparation position outside the instrument disc range of motion.

At a process 202, the control system may determine or sense if the bosses of the roll ISA disc have fully engaged the pockets of the instrument disc while the ISA disc is moving in the first rotational direction. More specifically, the control system may determine if the actuating element driving rotation of the ISA disc has experienced a resistance torque (e.g., a stall) due to the instrument disc encountering a hard stop, which is a physical limitation that prevents the engaged instrument and ISA discs from continued rotation. Each motor driving rotation of the ISA disc may have a unique torque threshold. A hard stop is indicated if the absolute value of the measured resistance torque is greater than the torque threshold for the specific motor. Encountering a hard stop is an indication that both bosses of the ISA have engaged the pockets of the instrument discs. Specific examples of the structures that may provide hard stops are described in U.S. Pat. App. No. 61/954,408 which was incorporated by reference above. For example, the instrument disc may include a protrusion. A protruding stopping mechanism along the rotational travel path of the protrusion may provide a physical limitation or hard stop when the protrusion is rotated into abutment with the stopping mechanism. In alternative embodiments, engagement of the instrument disc and ISA disc may be determined by other types of sensors such as optical sensors.

The actuator driving the first ISA disc may be preprogrammed to rotate the first ISA disc for a preprogrammed number of rotations in the first direction, according to a preprogrammed protocol. However, if the hard stop is encountered (i.e., engagement is determined) prior to the completion of the preprogrammed number of rotations in the first direction, the preprogrammed rotation in the first direction is aborted and the engagement procedure proceeds to process 210. Terminating the preprogrammed movement upon detection of engagement, may speed the overall engagement process.

At a process 204, if engagement of the roll ISA disc is not detected, the ISA roll disc is rotated in second rotational direction, opposite the first direction. For example, if the first rotational direction is clockwise, the second rotation direction is counter clockwise. At a process 206, the control system determines if the bosses of the roll ISA disc have fully engaged the pockets of the instrument disc while the ISA disc is moving in the second rotational direction. More specifically, the control system may determine if the actuating element driving rotation of the ISA disc has experienced a resistance torque (e.g., a stall) due to instrument disc encountering a hard stop. Encountering a hard stop is an indication that both bosses of the ISA disc have engaged the pockets of the instrument discs.

The actuator driving the first ISA disc may be preprogrammed to rotate the first ISA disc for a preprogrammed number of rotations in the second rotational direction, according to a preprogrammed protocol. However, if the hard stop is encountered (i.e., engagement is determined) prior to the completion of the preprogrammed number of rotations in the second direction, the preprogrammed rotation in the second direction is aborted and the engagement procedure proceeds to process 210. Terminating the preprogrammed movement upon detection of engagement, may speed the overall engagement process.

If the ISA roll disc has not engaged the instrument disc after rotation in both the first rotational direction and the second rotational direction, the process 201 may again be initiated. Optionally, at a process 208, the control system may count and limit the number of times the processes 201-206 may be repeated. After the count reaches the limit, the control system may provide the user an indication of failure to engage. If the user receives an indication that the instrument has failed to engage, the instrument may be detached from the ISA and reattached to begin the process 200 again.

After processes 202 and 206, if engagement is determined, engagement of one or more of the remaining ISA discs may be initiated. In this embodiment, at a process 210, multiple ISA discs are rotated in a first rotational direction. In this embodiment, the ISA discs rotated at process 210 may be the discs 108a, 108b, 108d, 108e associated with the control of yaw, pitch, and grip motions for the instrument wrist and surgical tool.

At a process 212, the control system may determine if the bosses for the yaw, pitch and grip ISA discs have fully engaged the pockets of the instrument discs while the ISA discs are moving in the first rotational direction. More specifically, the control system may determine if the actuating elements driving rotation of the ISA discs for yaw, pitch, and grip have experienced a resistance torque (e.g., a stall) due to instrument disc encountering a hard stop. Encountering a hard stop is an indication that both bosses of each ISA disc have engaged the pockets of the instrument discs.

The actuators driving the yaw, pitch and grip ISA discs may be preprogrammed to rotate the discs for a preprogrammed number of rotations in the first rotational direction, according to a preprogrammed protocol. However, if hard stops are encountered (i.e., engagement is determined) prior to the completion of the preprogrammed number of rotations in the first direction, the preprogrammed rotation in the first direction is aborted and the engagement procedure proceeds to process 220. Terminating the preprogrammed movement upon detection of engagement, may speed the overall engagement process.

At a process 214, if engagement of one or more of the ISA discs is not detected, the ISA disc(s) for which engagement is not detected is rotated in a second rotational direction, opposite the first direction. For example, if the first rotational direction is clockwise, the second rotation direction is counter clockwise. The ISA discs that are detected to be engaged at process 212 will not be rotated in the second rotational direction. They will generally be held still or moved only to compensate for the movement of the instrument caused by the discs that are continuing the engagement process. At a process 216, the control system determines if the bosses of the yaw, pitch, and grip ISA discs have fully engaged the pockets of the instrument discs while the ISA disc is moving in the second rotational direction. More specifically, the control system may determine if the actuating element driving rotation of the ISA disc has experienced a resistance torque (e.g., a stall) due to instrument disc encountering a hard stop. Encountering a hard stop is an indication that both bosses of the ISA have engaged the pockets of the instrument discs.

The actuators driving the yaw, pitch and grip ISA discs may be preprogrammed to rotate the discs for a preprogrammed number of rotations in the second rotational direction, according to a preprogrammed protocol. However, if hard stops are encountered (i.e., engagement is determined) prior to the completion of the preprogrammed number of rotations in the second direction, the preprogrammed rotation in the second direction is aborted and the engagement procedure proceeds to process 220. Terminating the preprogrammed movement upon detection of engagement, may speed the overall engagement process.

If the ISA discs have not engaged the instrument disc after rotation in both the first rotational direction and the second rotational direction, the process 210 may again be initiated. Optionally, the control system may count and limit the number of times the processes 210-216 may be repeated. After the count reaches the limit, the control system may provide the user an indication of failure to engage. If the user receives an indication that the instrument has failed to engage, the instrument may be detached from the ISA and reattached to begin the process 200 again.

In alternative embodiments, rather than performing parallel processes for engagement of the yaw, pitch, and grip discs, the engagement process for each disc may be performed in serial (e.g., similar to the processes 201-206 where only one disc is engaged at a time). In alternative embodiments, if multiple disc engagement procedures are performed in parallel (as in processes 210-216), the discs may have differing first rotational direction and differing second rotational directions. For example, the one of the discs associated with yaw, pitch, and grip movement may have a first clockwise rotational direction and a second counter clockwise direction, while another one of the discs associated with yaw, pitch, and grip movement may have a first counterclockwise rotational direction and a second clockwise rotational direction.

After processes 212 and 216, if engagement is determined, the successful and complete engagement of the instrument with the ISA may be confirmed and communicated to a user. After a successful engagement is confirmed, the instrument may be moved to an introductory position to begin the medical procedure. Further, the distal end of the instrument may be prevented from moving beyond the end of the cannula until after successful engagement is determined.

Figure 6:
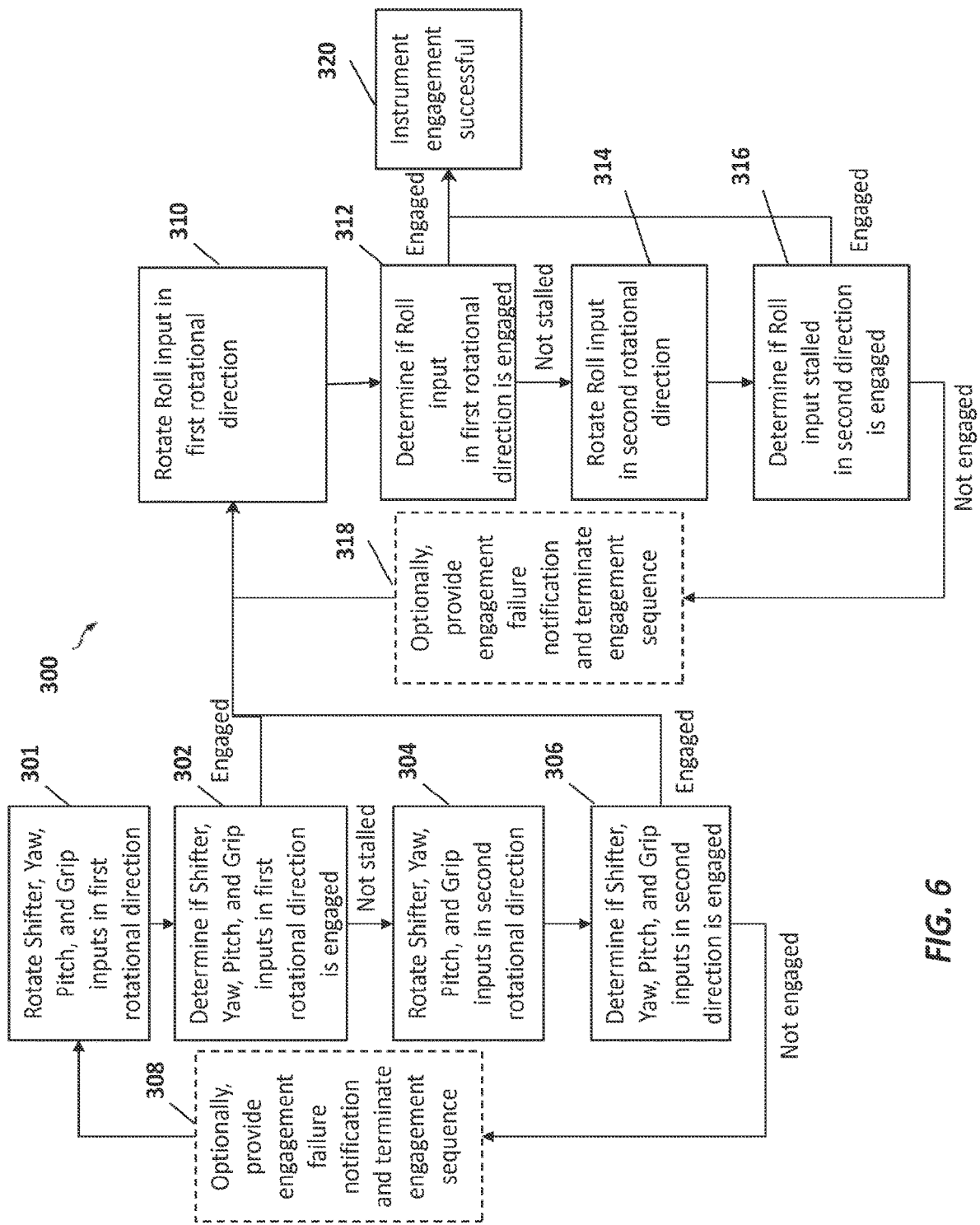
FIG. 6 is a flowchart showing an illustrative method for instrument engagement, according to one example of principles described herein.

FIG. 6 is a flowchart 300 showing another illustrative method for instrument engagement. The instrument engagement procedure is initiated after the proximal control portion of the instrument is attached to the ISA and the ISA discs are placed adjacent to the instrument discs. In this embodiment, the instrument to be engaged may be a stapler instrument, including for example the stapler instrument described in International App. No. PCT/US15/23636, filed Mar. 31, 2015) (disclosing "Surgical Instrument with Shiftable Transmission"), which is incorporated by reference herein in its entirety. The stapler instrument may include multiple instrument coupling discs (e.g., discs 110) driven by multiple carriage/ISA discs. For example, instrument discs for wrist motion (yaw and pitch) and grip motion may be similar to those previously described. In this embodiment, one of the instrument coupling discs is a shifter input disc and another instrument coupling disc is a drive output control disc. The shifter disc is used to select between three functions of the drive output, namely roll, clamp or fire. The shifter disc may also be used to lock the drive disc, which may lock the configuration of the drive disc during the instrument installation. In this embodiment, the shifter disc engagement procedure is performed prior to the drive disc engagement procedure. This ensures that the shifter is engaged before engaging the drive disc. With existing systems, if the shifter is not engaged, the system may proceed with engaging the drive disc. The system would mistakenly believe that a roll hard stop was encountered when, actually, the instrument was just encountering the resistance of the lock. This would cause the roll position to be registered to the wrong location and cause subsequent non-intuitive motion.

At a process 301, multiple ISA discs are rotated in a first rotational direction. In this embodiment, the ISA discs rotated at process 301 may be the discs associated with the control of wrist movement (i.e., yaw, pitch), grip motion for the surgical tool, and shifter motion. In alternative embodiments, rather than performing parallel (i.e., simultaneous) processes for engagement of the yaw, pitch, grip, and shifter discs, the engagement process for each disc may be performed in serial. If the multiple disc engagement procedures are performed in parallel, the discs may have differing first rotational direction and differing second rotational directions and/or may have differing rates of rotation.

At a process 302, the control system may determine if the bosses for the yaw, pitch, grip, and shifter ISA discs have fully engaged the pockets of the instrument disc while the ISA discs are moving in the first rotational direction. More specifically, the control system may determine if the actuating elements driving rotation of the ISA discs have experienced a resistance torque (e.g., a stall) due to instrument disc encountering a hard stop. Encountering a hard stop is an indication that both bosses of each ISA disc have engaged the pockets of the instrument discs.

The actuators driving the shifter, yaw, pitch and grip ISA discs may be preprogrammed to rotate the discs for a preprogrammed number of rotations in the first rotational direction, according to a preprogrammed protocol. However, if hard stops are encountered (i.e., engagement is determined) prior to the completion of the preprogrammed number of rotations in the first direction, the preprogrammed rotation in the first direction is aborted and the engagement procedure proceeds to process 310. Terminating the preprogrammed movement upon detection of engagement, may speed the overall engagement process.

At a process 304, if engagement of one or more of the ISA discs is not detected, the ISA disc(s) for which engagement is not detected is rotated in a second rotational direction, opposite the first direction. For example, if the first rotational direction is clockwise, the second rotation direction is counter clockwise. The ISA discs that are detected to be engaged at process 302 will not be rotated in the second rotational direction. At a process 306, the control system determines if the bosses of the yaw, pitch, grip, and shifter ISA disc have fully engaged the pockets of the instrument disc while the ISA disc is moving in the second rotational direction. More specifically, the control system may determine if the actuating element driving rotation of the ISA discs have experienced a resistance torque (e.g., a stall) due to instrument disc(s) encountering a hard stop. Encountering a hard stop is an indication that both bosses of the ISA have engaged the pockets of the instrument discs.

The actuators driving the yaw, pitch and grip ISA discs may be preprogrammed to rotate the discs for a preprogrammed number of rotations in the second rotational direction, according to a preprogrammed protocol. However, if hard stops are encountered (i.e., engagement is determined) prior to the completion of the preprogrammed number of rotations in the second direction, the preprogrammed rotation in the second direction is aborted and the engagement procedure proceeds to process 310. Terminating the preprogrammed movement upon detection of engagement, may speed the overall engagement process.

If the ISA discs have not engaged the instrument disc after rotation in both the first rotational direction and the second rotational direction, the process 301 may again be initiated.

Optionally, at process 308, the control system may count and limit the number of times the processes 301-306 may be repeated. After the count reaches the limit, the control system may provide the user an indication of failure to engage. If the user receives an indication that the instrument has failed to engage, the instrument may be detached from the ISA and reattached to begin the process 300 again.

After processes 302 and 306, if engagement is determined, engagement of one or more of the remaining ISA discs may be initiated. In this embodiment, the engaged shifter is moved to select the roll mode. At a process 310, the roll ISA disc is rotated in a first rotational direction.

At a process 312, the control system may determine if the bosses for the roll ISA disc have fully engaged the pockets of the instrument disc while the ISA disc is moving in the first rotational direction. More specifically, the control system may determine if the actuating element driving rotation of the ISA disc for roll has experienced a resistance torque (e.g., a stall) due to instrument disc encountering a hard stop. Encountering a hard stop is an indication that both bosses of the roll ISA disc have engaged the pockets of the instrument disc.

The actuators driving the roll ISA disc may be preprogrammed to rotate the disc for a preprogrammed number of rotations in the first rotational direction, according to a preprogrammed protocol. However, if a hard stop is encountered (i.e., engagement is determined) prior to the completion of the preprogrammed number of rotations in the first direction, the preprogrammed rotation in the first direction is aborted and the engagement procedure proceeds to process 320. Terminating the preprogrammed movement upon detection of engagement, may speed the overall engagement process.

At a process 314, if engagement of the roll ISA discs is not detected, the roll ISA disc is rotated in a second rotational direction, opposite the first direction. For example, if the first rotational direction is clockwise, the second rotation direction is counter clockwise. At a process 316, the control system determines if the bosses of the roll ISA disc have fully engaged the pockets of the instrument disc while the ISA disc is moving in the second rotational direction. More specifically, the control system may determine if the actuating element driving rotation of the ISA disc has experienced a resistance torque (e.g., a stall) due to instrument disc encountering a hard stop. Encountering a hard stop is an indication that both bosses of the ISA disc have engaged the pockets of the instrument disc.

The actuators driving the roll ISA disc may be preprogrammed to rotate the disc for a preprogrammed number of rotations in the second rotational direction, according to a preprogrammed protocol. However, if a hard stop is encountered (i.e., engagement is determined) prior to the completion of the preprogrammed number of rotations in the second direction, the preprogrammed rotation in the second direction is aborted and the engagement procedure proceeds to process 320. Terminating the preprogrammed movement upon detection of engagement, may speed the overall engagement process.

If the ISA roll disc has not engaged the instrument disc after rotation in both the first rotational direction and the second rotational direction, the process 310 may again be initiated. Optionally, a process. 318, the control system may count and limit the number of times the processes 310-316 may be repeated. After the count reaches the limit, the control system may provide the user an indication of failure to engage. If the user receives an indication that the instrument has failed to engage, the instrument may be detached from the ISA and reattached to begin the process 300 again.

After processes 312 and 316, if engagement is determined, the successful and complete engagement of the instrument with the ISA may be confirmed and communicated to a user. After a successful engagement is confirmed, the stapler may be moved to an introductory position to begin the medical procedure. Further, the distal end of the instrument may be prevented from moving beyond the end of the cannula until after successful engagement is determined.

Figure 7:
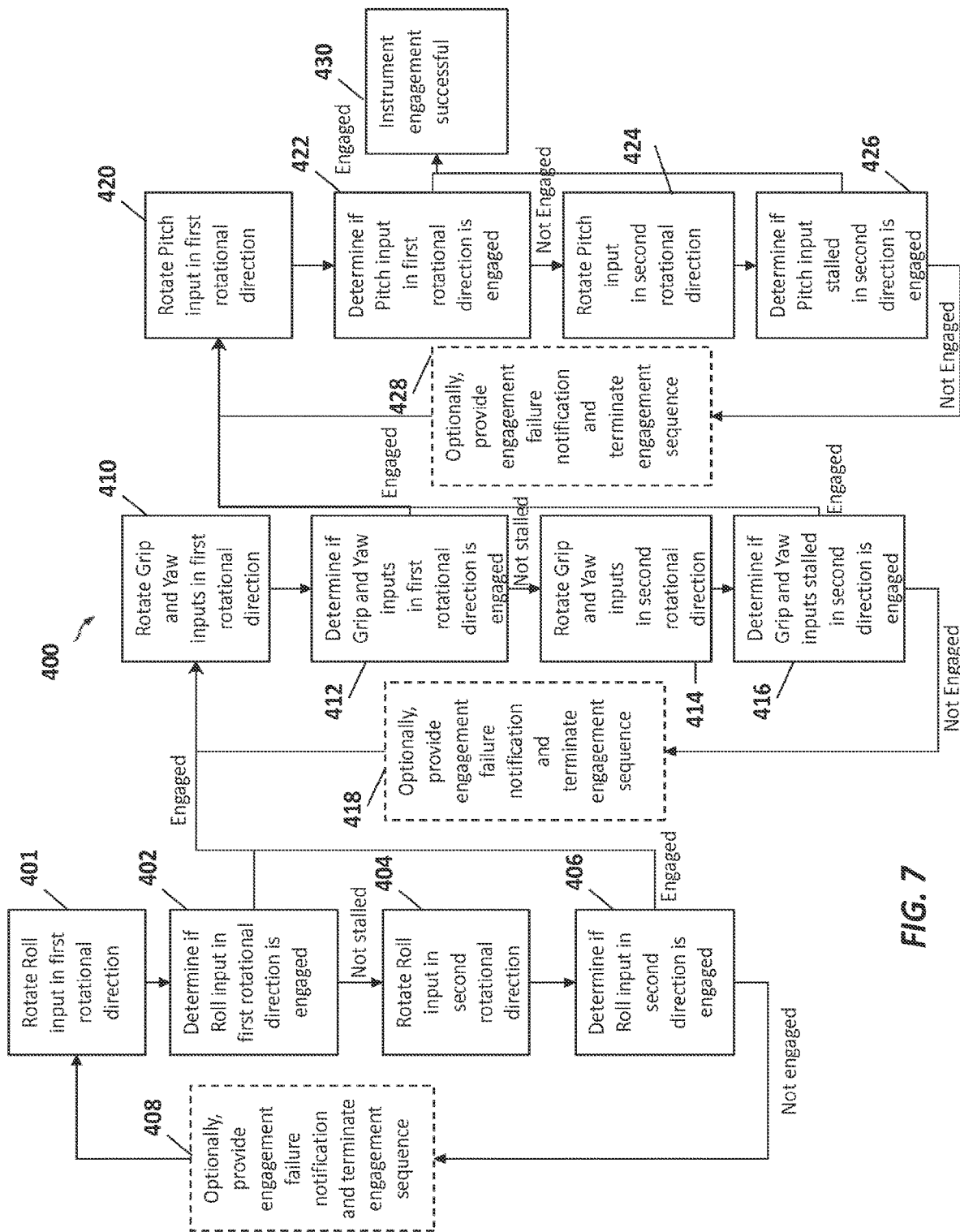
FIG. 7 is a flowchart showing an illustrative method for instrument engagement, according to one example of principles described herein.

FIG. 7 is a flowchart 400 showing another illustrative method for instrument engagement. The instrument engagement procedure is initiated after the proximal control portion of the instrument is attached to the ISA and the ISA discs are placed adjacent to the instrument discs. In this embodiment, the instrument to be engaged may be a clip applier. The clip applier may receive a clip (e.g., a v-shaped piece of metal or polymer) that fits between jaws of the clip applier. The clip applier squeezes the clip onto a blood vessel to seal the vessel. The clip may include a latch that holds the clip closed after it is squeezed by the clip applier. If the clip is prematurely squeezed, it can fall out of the clip applier and into the patient. Premature squeezing of the clip may occur if one of the grip discs on the instrument are not fully engaged before engaging the disc(s) associated with pitch. The movement in the pitch direction may squeeze the jaw into the cannula and deform the clip. The below described engagement procedure is designed to avoid squeezing the clip during the engagement process.

At a process 401, a first ISA disc is rotated in a first rotational direction. In this embodiment, the first ISA disc may be the disc associated with the control of roll motion for the instrument shaft. In alternative embodiments, the ISA may be omitted and the carriage drive discs may directly engage the instrument discs using the described engagement procedures. During process 401, as the roll ISA disc is rotated in the first rotational direction, the other ISA discs (e.g., those controlling yaw, pitch, and grip) are unengaged. They may, for example, be outside the instrument disc range of motion and/or movable to a preparation position outside the instrument disc range of motion.

At a process 402, the control system may determine or sense if the bosses of the roll ISA disc have fully engaged the pockets of the instrument disc while the ISA disc is moving in the first rotational direction. More specifically, the control system may determine if the actuating element driving rotation of the ISA disc has experienced a resistance torque (e.g., a stall) due to the instrument disc encountering a hard stop, which is a physical limitation that prevents the engaged instrument and ISA discs from continued rotation.

The actuator driving the roll ISA disc may be preprogrammed to rotate the disc for a preprogrammed number of rotations in the first rotational direction, according to a preprogrammed protocol. However, if a hard stop is encountered (i.e., engagement is determined) prior to the completion of the preprogrammed number of rotations in the first direction, the preprogrammed rotation in the first direction is aborted and the engagement procedure proceeds to process 410. Terminating the preprogrammed movement upon detection of engagement, may speed the overall engagement process.

At a process 404, if engagement of the roll ISA disc is not detected, the ISA roll disc is rotated in second rotational direction, opposite the first direction. For example, if the first rotational direction is clockwise, the second rotation direction is counter clockwise. At a process 406, the control system determines if the bosses of the roll ISA disc have fully engaged the pockets of the instrument disc while the ISA disc is moving in the second rotational direction. More specifically, the control system may determine if the actuating element driving rotation of the ISA disc has experienced a resistance torque (e.g., a stall) due to instrument disc encountering a hard stop. Encountering a hard stop is an indication that both bosses of the ISA disc have engaged the pockets of the instrument discs.

The actuator driving the roll ISA disc may be preprogrammed to rotate the disc for a preprogrammed number of rotations in the second rotational direction, according to a preprogrammed protocol. However, if a hard stop is encountered (i.e., engagement is determined) prior to the completion of the preprogrammed number of rotations in the second direction, the preprogrammed rotation in the first direction is aborted and the engagement procedure proceeds to process 410. Terminating the preprogrammed movement upon detection of engagement, may speed the overall engagement process.

If the ISA roll disc has not engaged the instrument disc after rotation in both the first rotational direction and the second rotational direction, the process 401 may again be initiated. Optionally, at a process 408, the control system may count and limit the number of times the processes 401-406 may be repeated. After the count reaches the limit, the control system may provide the user an indication of failure to engage. If the user receives an indication that the instrument has failed to engage, the instrument may be detached from the ISA and reattached to begin the process 400 again.

After processes 402 and 406, if engagement is determined, engagement of one or more of the remaining ISA discs may be initiated. In this embodiment, at a process 410, multiple ISA discs are rotated in a first rotational direction. In this embodiment, the ISA discs rotated at process 210 may be the discs associated with the control of yaw and grip motions for the instrument wrist and surgical tool. The discs associated with yaw and grip, in this and other embodiments, may be coupled in that separate discs move each opposable finger member of the grip. When the finger members are moved in opposite directions gripping and release of grip occurs. When the fingers are moved together, the yaw motion occurs.

At a process 412, the control system may determine if the bosses for the yaw and grip ISA discs have fully engaged the pockets of the instrument discs while the ISA discs are moving in the first rotational direction. More specifically, the control system may determine if the actuating elements driving rotation of the ISA discs for yaw and grip have experienced a resistance torque (e.g., a stall) due to instrument disc encountering a hard stop. Encountering a hard stop is an indication that both bosses of each ISA disc have engaged the pockets of the instrument discs.

The actuators driving the grip and yaw ISA discs may be preprogrammed to rotate the disc for a preprogrammed number of rotations in the first rotational direction, according to a preprogrammed protocol. However, if a hard stop is encountered (i.e., engagement is determined) prior to the completion of the preprogrammed number of rotations in the first direction, the preprogrammed rotation in the first direction is aborted and the engagement procedure proceeds to process 420. Terminating the preprogrammed movement upon detection of engagement, may speed the overall engagement process.

At a process 414, if engagement of one or more of the ISA discs is not detected, the ISA disc(s) for which engagement is not detected is rotated in a second rotational direction, opposite the first direction. For example, if the first rotational direction is clockwise, the second rotation direction is counter clockwise. The ISA discs that are detected to be engaged at process 412 will not be rotated in the second rotational direction. At a process 416, the control system determines if the bosses of the yaw and grip ISA discs have fully engaged the pockets of the instrument discs while the ISA disc is moving in the second rotational direction. More specifically, the control system may determine if the actuating element driving rotation of the ISA disc has experienced a resistance torque (e.g., a stall) due to instrument disc encountering a hard stop. Encountering a hard stop is an indication that both bosses of the ISA have engaged the pockets of the instrument discs.

The actuators driving the grip and yaw ISA discs may be preprogrammed to rotate the disc for a preprogrammed number of rotations in the second rotational direction, according to a preprogrammed protocol. However, if a hard stop is encountered (i.e., engagement is determined) prior to the completion of the preprogrammed number of rotations in the second direction, the preprogrammed rotation in the second direction is aborted and the engagement procedure proceeds to process 420. Terminating the preprogrammed movement upon detection of engagement, may speed the overall engagement process.

If the ISA discs have not engaged the instrument disc after rotation in both the first rotational direction and the second rotational direction, the process 410 may again be initiated. Optionally, the control system may count and limit the number of times the processes 410-416 may be repeated. After the count reaches the limit, the control system may provide the user an indication of failure to engage. If the user receives an indication that the instrument has failed to engage, the instrument may be detached from the ISA and reattached to begin the process 400 again.

After processes 412 and 416, if engagement is determined, engagement of one or more of the remaining ISA discs may be initiated. In this embodiment, at a process 420, one or more ISA discs for driving pitch motion are rotated in a first rotational direction.

At a process 422, the control system may determine if the bosses for the pitch ISA disc(s) have fully engaged the pockets of the instrument disc while the ISA disc is moving in the first rotational direction. More specifically, the control system may determine if the actuating elements driving rotation of the ISA disc(s) for pitch have experienced a resistance torque (e.g., a stall) due to instrument disc encountering a hard stop. Encountering a hard stop is an indication that both bosses of each ISA disc have engaged the pockets of the instrument discs.

The actuator(s) driving the pitch ISA discs may be preprogrammed to rotate the disc for a preprogrammed number of rotations in the first rotational direction, according to a preprogrammed protocol. However, if a hard stop is encountered (i.e., engagement is determined) prior to the completion of the preprogrammed number of rotations in the first direction, the preprogrammed rotation in the first direction is aborted and the engagement procedure proceeds to process 430. Terminating the preprogrammed movement upon detection of engagement, may speed the overall engagement process.

At a process 424, if engagement of the pitch ISA disc is not detected, the pitch ISA disc is rotated in a second rotational direction, opposite the first direction. For example, if the first rotational direction is clockwise, the second rotation direction is counter clockwise. At a process 426, the control system determines if the bosses of the pitch ISA disc have fully engaged the pockets of the instrument disc while the ISA disc is moving in the second rotational direction. More specifically, the control system may determine if the actuating element driving rotation of the ISA disc has experienced a resistance torque (e.g., a stall) due to instrument disc encountering a hard stop. Encountering a hard stop is an indication that both bosses of the ISA have engaged the pockets of the instrument disc.

The actuator(s) driving the pitch ISA discs may be preprogrammed to rotate the disc for a preprogrammed number of rotations in the second rotational direction, according to a preprogrammed protocol. However, if a hard stop is encountered (i.e., engagement is determined) prior to the completion of the preprogrammed number of rotations in the second direction, the preprogrammed rotation in the first direction is aborted and the engagement procedure proceeds to process 430. Terminating the preprogrammed movement upon detection of engagement, may speed the overall engagement process.

If the ISA discs have not engaged the instrument disc after rotation in both the first rotational direction and the second rotational direction, the process 420 may again be initiated. Optionally, the control system may count and limit the number of times the processes 420-426 may be repeated. After the count reaches the limit, the control system may provide the user an indication of failure to engage. If the user receives an indication that the instrument has failed to engage, the instrument may be detached from the ISA and reattached to begin the process 400 again.

After processes 422 and 426, if engagement is determined, the successful and complete engagement of the instrument with the ISA may be confirmed and communicated to a user. After a successful engagement is confirmed, the clip applier may be moved to an introductory position to begin the medical procedure. Further, the distal end of the instrument may be prevented from moving beyond the end of the cannula until after successful engagement is determined.

One or more elements in embodiments of the invention may be implemented in software to execute on a processor of a computer system such as a control processing system. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disc, a hard disc, or other storage device, the code segments may be downloaded via computer networks such as the Internet, Intranet, etc.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A medical system comprising:
    a control system having one or more processors; and
    an instrument manipulator configured to receive an instrument, the instrument manipulator including a first drive output and a first actuating element configured to drive movement of the first drive output, the first drive output configured to drive a first input coupling of the instrument;
    wherein the control system is configured to:
        receive an indication that the first input coupling of the instrument is positioned adjacent to the first drive output of the manipulator;
        in response to receiving the indication, command the first actuating element to cause movement of the first drive output;
        receive a feedback associated with a force experienced by the first actuating element during the movement of the first drive output;
        determine an instruction signal for the first actuating element based on the feedback; and
        transmit the instruction signal to the first actuating element.

2. The medical system of claim 1, wherein the movement is a rotation, and the force is a torque.

3. The medical system of claim 1, wherein the control system is configured to determine the instruction signal for the first actuating element based on the feedback by:
    determining whether the first drive output has engaged the first input coupling based on the feedback.

4. The medical system of claim 1, wherein the control system is configured to determine the instruction signal for the first actuating element based on the feedback by:
    in response to the feedback indicating that a resistance is experienced by the first actuating element during the movement, determining the instruction signal to command the actuating element to abort the movement.

5. The medical system of claim 1, wherein:
    the control system is configured to command the first actuating element to cause the movement of the first drive output by: causing movement of the first drive output according to a preprogrammed protocol; and
    the control system is configured to determine the instruction signal for the first actuating element based on the feedback by: in response to a resistance being experienced by the first actuating element during the movement, determining the instruction signal for terminating the preprogrammed protocol.

6. The medical system of claim 1, wherein the control system is configured to determine the instruction signal for the first actuating element based on the feedback by:
    in response to the feedback indicating that a resistance is not experienced by the first actuating element during the movement, determining the instruction signal to command the actuating element to move the first drive output in a second direction, wherein the movement is in a first direction, and wherein the second direction differs from the first direction.

7. The medical system of claim 1, wherein the control system is configured to determine the instruction signal for the first actuating element based on the feedback by:
   determining the first drive output has engaged the first input coupling by comparing the feedback to a first threshold.

8. The medical system of claim 7, wherein one of the first input coupling or the first drive output includes a protrusion, wherein the other of the first input coupling or the first drive output includes a pocket, and wherein the first threshold is associated with a physical engagement of the protrusion with the pocket.

9. The medical system of claim 7, wherein the first threshold is associated with a stall to the movement caused by a hard stop.

10. The medical system of claim 1, wherein:
    the instrument manipulator comprises a second drive output configured to engage a second input coupling of the instrument, wherein movement of the first input coupling moves the instrument in a first degree of freedom, and wherein movement of the second input coupling moves the instrument in a second degree of freedom; and
    the instrument manipulator comprises a second actuating element configured to drive movement of the second drive output; and
    the control system is further configured to:
        in response to receiving the indication, command the first actuating element to cause movement of the second drive output;
        receive second feedback associated with a force experienced during movement of the second drive output;
        determine a second instruction signal for the second actuating element based on the second feedback; and
        transmit the second instruction signal to the second actuating element.

11. The medical system of claim 10, wherein the instrument includes a shaft and a joint, wherein the first degree of freedom is a roll of the shaft, and wherein the second degree of freedom is movement of the joint.

12. The medical system of claim 10, wherein the instrument includes a shaft, a first joint along the shaft, and a second joint along the shaft, wherein the first degree of freedom is movement of the first joint, and wherein the second degree of freedom is movement of the second joint.

13. A method of operating a medical system comprising a control system having one or more processors, an instrument, and an instrument manipulator configured to receive the instrument, the method comprising:
    receiving an indication that a first input coupling of the instrument is positioned adjacent to a first drive output of the manipulator, wherein the first drive output is configured to drive a first input coupling of the instrument;
    in response to receiving the indication, commanding a first actuating element of the manipulator to cause movement of the first drive output;
    receiving a feedback associated with a force experienced by the first drive output during the movement of the first drive output;
    determining an instruction signal for the first actuating element based on the feedback; and
    transmitting the instruction signal to the first actuating element.

14. The method of claim 13, wherein the movement is a rotation, and the force is a torque.

15. The method of claim 13, wherein determining an instruction signal for the first actuating element based on the feedback comprises:
    determining whether the first drive output has engaged the first input coupling based on the feedback.

16. The method of claim 13, wherein determining the instruction signal for the first actuating element based on the feedback comprises:
    in response to the feedback indicating that a resistance is experienced by the first actuating element during the movement, determining the instruction signal to command the actuating element to abort the movement.

17. The method of claim 13, wherein
    commanding the first actuating element to cause the movement of the first drive output comprises: causing movement of the first drive output according to a preprogrammed protocol; and
    determining the instruction signal for the first actuating element based on the feedback comprises: in response to a resistance being experienced by the first actuating element during the movement, determining the instruction signal for terminating the preprogrammed protocol.

18. The method of claim 13, wherein determining the instruction signal for the first actuating element based on the feedback comprises:
    in response to the feedback indicating that a resistance is not experienced by the first actuating element during the movement, determining the instruction signal to command the actuating element to move the first drive output in a second direction, wherein the movement is in a first direction, and wherein second direction differs from the first direction.

19. A non-transitory machine-readable medium comprising a plurality of machine-readable instructions which, when executed by one or more processors associated with a medical system comprising an instrument manipulator, are adapted to cause the one or more processors to perform a method comprising:
    receiving an indication that a first input coupling of the instrument is positioned adjacent to a first drive output of the manipulator, wherein the first drive output is configured to drive a first input coupling of the instrument;
    in response to receiving the indication, commanding a first actuating element of the manipulator to cause movement of the first drive output;
    receiving a feedback associated with a force experienced by the first actuating element during the movement of the first drive output;
    determining an instruction signal for the first actuating element based on the feedback; and
    transmitting the instruction signal to the first actuating element.

20. The non-transitory machine-readable medium of claim 19, wherein determining an instruction signal for the first actuating element based on the feedback comprises:
    in response to the feedback indicating that a resistance is experienced by the first actuating element during the movement, determining the instruction signal to command the actuating element to abort the movement; or
    in response to the feedback indicating that a resistance is not experienced by the first actuating element during the movement, determining the instruction signal to command the actuating element to move the first drive output in a second direction, wherein the movement is in a first direction, and wherein the second direction differs from the first direction.

21. The non-transitory machine-readable medium of claim 19, wherein:
commanding the first actuating element to cause the movement of the first drive output comprises: causing movement of the first drive output according to a preprogrammed protocol; and
determining the instruction signal for the first actuating element based on the feedback comprises: in response to a resistance being experienced by the first actuating element during the movement, determining the instruction signal for terminating the preprogrammed protocol.

* * * * *